United States Patent
Biris

(10) Patent No.: US 9,968,711 B2
(45) Date of Patent: May 15, 2018

(54) BONE REGENERATION USING BIODEGRADABLE POLYMERIC NANOCOMPOSITE MATERIALS AND APPLICATIONS OF THE SAME

(71) Applicant: BOARD OF TRUSTEES OF THE UNIVERSITY OF ARKANSAS, Little Rock, AR (US)

(72) Inventor: Alexandru S. Biris, Little Rock, AR (US)

(73) Assignee: BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 65 days.

(21) Appl. No.: 15/220,727

(22) Filed: Jul. 27, 2016

(65) Prior Publication Data
US 2016/0331869 A1 Nov. 17, 2016

Related U.S. Application Data

(60) Continuation of application No. 14/506,438, filed on Oct. 3, 2014, now Pat. No. 9,427,497, which is a division of application No. 13/947,770, filed on Jul. 22, 2013, now Pat. No. 8,936,805, which is a continuation-in-part of application No. 11/519,316, filed on Sep. 11, 2006, now Pat. No. 8,518,123.

(60) Provisional application No. 60/715,841, filed on Sep. 9, 2005, provisional application No. 60/726,383, filed on Oct. 13, 2005, provisional application No. 61/800,588, filed on Mar. 15, 2013.

(51) Int. Cl.
| | |
|---|---|
| *A61F 2/28* | (2006.01) |
| *A61L 27/36* | (2006.01) |
| *A61L 27/38* | (2006.01) |
| *A61L 27/44* | (2006.01) |
| *A61L 27/46* | (2006.01) |
| *A61L 27/58* | (2006.01) |
| *A61L 27/56* | (2006.01) |
| *A61L 27/50* | (2006.01) |
| *A61L 27/54* | (2006.01) |

(52) U.S. Cl.
CPC ............... *A61L 27/58* (2013.01); *A61F 2/28* (2013.01); *A61F 2/2846* (2013.01); *A61L 27/365* (2013.01); *A61L 27/3608* (2013.01); *A61L 27/38* (2013.01); *A61L 27/44* (2013.01); *A61L 27/46* (2013.01); *A61L 27/50* (2013.01); *A61L 27/54* (2013.01); *A61L 27/56* (2013.01); *A61F 2002/2835* (2013.01); *A61L 2300/412* (2013.01); *A61L 2300/414* (2013.01); *A61L 2300/64* (2013.01); *A61L 2400/12* (2013.01); *A61L 2400/18* (2013.01); *A61L 2430/02* (2013.01); *Y10T 156/1062* (2015.01); *Y10T 156/1075* (2015.01)

(58) Field of Classification Search
CPC .. A61L 27/46; C08L 5/00; C08L 67/04; A61F 2002/2835; A61F 2/28
See application file for complete search history.

(56) References Cited

U.S. PATENT DOCUMENTS

| | | | | |
|---|---|---|---|---|
| 5,766,247 A | * | 6/1998 | Aoki ....................... | A61L 27/46 424/423 |
| 2007/0061015 A1 | * | 3/2007 | Jensen .................... | A61L 27/44 623/23.51 |

* cited by examiner

*Primary Examiner* — Alma Pipic
(74) *Attorney, Agent, or Firm* — Tim Tingkang Xia, Esq.; Locke Lord LLP

(57) ABSTRACT

A method of treating bone deficiencies includes applying a biocompatible structure to an implant surgical site. The biocompatible structure includes multiple polymer layers stacked to have a predetermined shape, multiple bone particle layers disposed between each of two neighboring polymer layers of the multiple polymer layers, and a coating surrounding the polymer layers and bone particle layers. Each of the polymer layers is formed with a polymer and first tissue forming nanoparticles. The predetermined shape is configured to conform to the implant surgical site.

13 Claims, 9 Drawing Sheets

BONE REGENERATION USING BIODEGRADABLE POLYMERIC NANOCOMPOSITE MATERIALS AND APPLICATIONS OF THE SAME

CROSS-REFERENCE TO RELATED PATENT APPLICATIONS

This application is a continuation of U.S. patent application Ser. No. 14/506,438, filed on Oct. 3, 2014, which itself is a divisional of, and claims benefit of U.S. patent application Ser. No. 13/947,770 (hereinafter, the '770 application), filed on Jul. 22, 2013, now U.S. Pat. No. 8,936,805. The '770 application is a continuation-in-part of U.S. patent application Ser. No. 11/519,316, filed on Sep. 11, 2006, now U.S. Pat. No. 8,518,123 and itself claims priority and the benefit of U.S. provisional application Ser. No. 60/715,841, filed on Sep. 9, 2005, and U.S. provisional application Ser. No. 60/726,383, filed on Oct. 13, 2005. The '770 application also claims priority and the benefit of U.S. provisional application Ser. No. 61/800,588, filed on Mar. 15, 2013. The entire contents of the above identified applications are incorporated herein by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

STATEMENT OF FEDERALLY-SPONSORED RESEARCH

This disclosure was made with Government support under Grant No. W81XWH-10-2-0130 awarded by the U.S. Department of Defense. The Government has certain rights in the disclosure.

FIELD

The present disclosure relates generally to a method of treating bone deficiencies, and more particularly to applying a biocompatible structure to an implant surgical site, where the biocompatible structure has a layered structure.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Skeletal deficiencies from trauma, tumors and bone diseases, or abnormal development frequently require surgical procedures to attempt to restore normal bone function. Although most of these treatments are successful, they all have problems and limitations.

Therefore, a heretofore unaddressed need exists in the art to address the aforementioned deficiencies and inadequacies.

SUMMARY

Certain aspects of the present disclosure are directed to method to treat bone deficiencies.

In certain embodiments, a method to treat bone deficiencies includes applying a biocompatible structure to an implant surgical site. The biocompatible structure includes a plurality of polymer layers stacked to have a predetermined shape, wherein each of the polymer layers is formed with a polymer and first tissue forming nanoparticles; a plurality of bone particle layers disposed between each of two neighboring polymer layers of the plurality of polymer layers; and a coating surrounding the plurality of polymer layers and bone particle layers.

In certain embodiments, the predetermined shape is configured to conform to the implant surgical site.

In certain embodiments, a weight percentage of the first tissue forming nanoparticles to the polymer is about 0.05-95% such that a resorption rate of the biocompatible structure substantially matches a rate of tissue generation in the biocompatible structure.

In certain embodiments, the weight percentage of the first tissue forming nanoparticles to the polymer is about 20%.

In certain embodiments, the weight percentage of the first tissue forming nanoparticles to the polymer is about 25%.

In certain embodiments, the polymer comprises a synthetic biodegradable polymer, a biodegradable polymer from a natural source, or a mixture thereof. The synthetic biodegradable polymer comprises polyurethane, polylactide (PLA), polyglycolide (PGA), poly(lactide-co-glycolide) (PLGA), poly(e-caprolactone), polydioxanone, polyanhydride, trimethylene carbonate, poly($\beta$-hydroxybutyrate), poly(g-ethyl glutamate), poly(desaminotyrosyl-tyrosine-hexyl ester (DTH)iminocarbonate), poly(bisphenol A iminocarbonate), poly(ortho ester), polycyanoacrylate, polyphosphazene, or a mixture thereof.

In certain embodiments, the first tissue forming nanoparticles comprise nanoparticles of hydroxypatites, tricalcium phosphates, mixed calcium phosphates and calcium carbonate, bone particles of zenograft, bone particles of allografts, bone particles of autografts, bone particles of alloplastic grafts, or a mixture thereof.

In certain embodiments, the biocompatible structure further comprises a plurality of second tissue forming particles attached to an outer surface of the coating.

In certain embodiments, the biocompatible structure is formed by: dissolving the polymer in a solvent to form a first solution; adding the first tissue forming nanoparticles to the first solution to form a second solution wherein a weight percentage of the first tissue forming nanoparticles to the polymer is about 0.01-95%; applying the second solution to a surface to form a polymer film on the surface, wherein the first tissue forming nanoparticles are dispersed in the polymer film;—dividing the polymer film into a plurality of strips; constructing a scaffold by stacking the strips to form polymer layers and adding bone or composite particles between the polymer layers; applying the second solution to the scaffold to form the coat layer surrounding the scaffold; and adding the second tissue forming particles to the coat layer to form a second tissue forming particle layer surrounding the coat layer, so as to obtain the biocompatible structure.

In certain embodiments, the biocompatible structure is further formed by, after adding the second tissue forming particles to the coat layer, plasma treating the-scaffold surrounded with the coat layer and the second tissue forming particle layer.

In certain embodiments, the surface is a polytetrafluoroethylene (PTFE) surface.

In certain embodiments, the second tissue forming particles comprise nano-sized bone particles, micro-sized bone particles, or a mixture thereof.

In certain embodiments, each of the strips has a length of about 0.005-50 centimeter, a width of about 0.002-50 centimeter, and a thickness of about 0.001-500 millimeter, and the biocompatible structure is in a cylindrical shape or a spherical shape.

In certain embodiments, the biocompatible structure is further formed by, adding a third tissue forming material to the biocompatible structure. The third tissue forming material comprises a bioactive material, cells, or a mixture thereof. The bioactive material comprises proteins, enzymes, growth factors, amino acids, bone morphogenic proteins, platelet derived growth factors, vascular endothelial growth factors, or a mixture thereof. The cells comprises epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof.

BRIEF DESCRIPTION OF THE DRAWINGS

The accompanying drawings illustrate one or more embodiments of the disclosure and, together with the written description, serve to explain the principles of the disclosure. The same reference numbers may be used throughout the drawings to refer to the same or like elements in the embodiments.

DETAILED DESCRIPTION

Figure 1A:
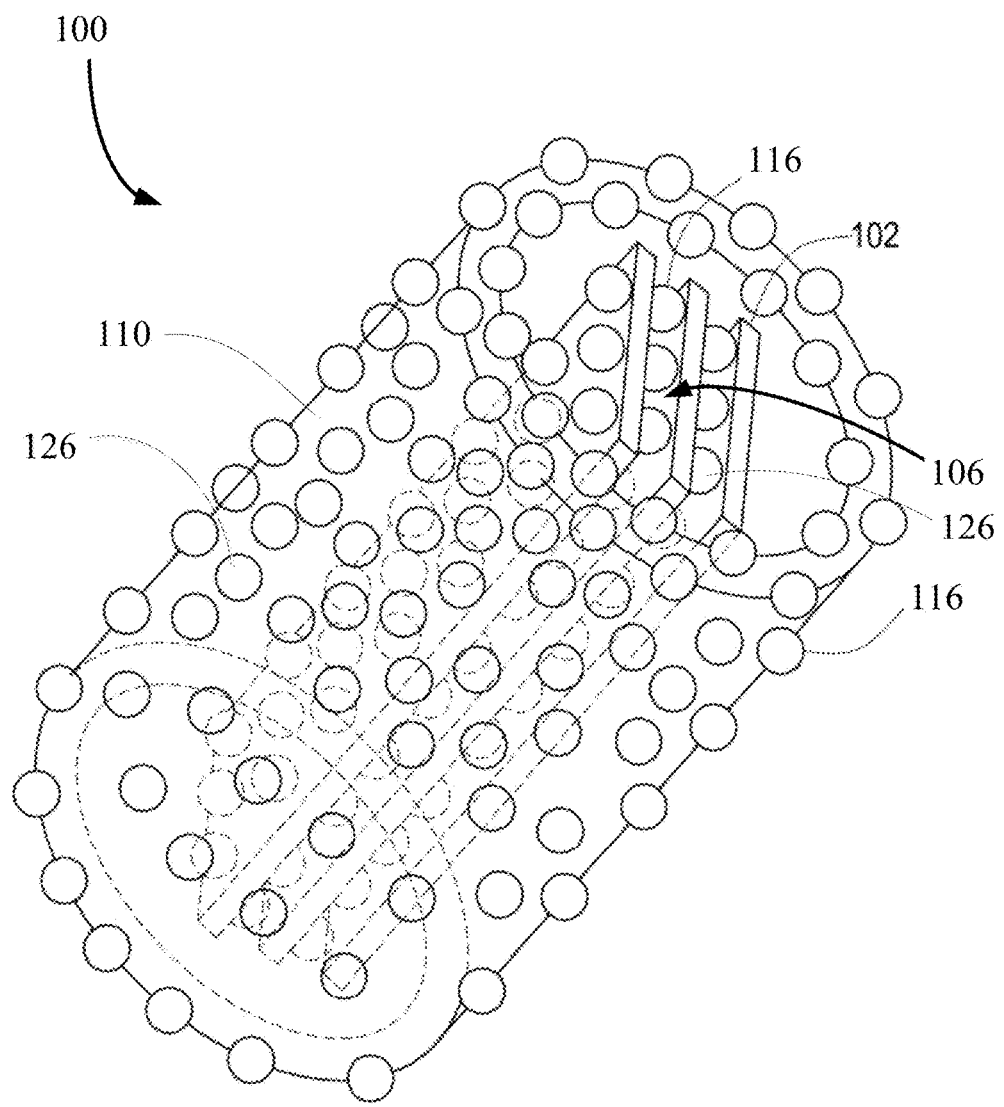
FIG. 1A illustrates a biocompatible structure according to certain embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the disclosure. Additionally, some terms used in this specification are more specifically defined below.

Typically, terms such as "first", "second", "third", and the like are used for distinguishing various elements, members, regions, layers, and areas from others. Therefore, the terms such as "first", "second", "third", and the like do not limit the number of the elements, members, regions, layers, areas, or the like. Further, for example, the term "first" can be replaced with the term "second", "third", or the like.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

Typically, "nanoscopic-scale," "nanoscopic," "nanometer-scale," "nanoscale," the "nano-" prefix, and the like refers to elements or articles having widths or diameters of less than about 1 μm, preferably less than about 100 nm in some cases. Specified widths can be smallest width (i.e. a width as specified where, at that location, the article can have a larger width in a different dimension), or largest width (i.e. where, at that location, the article's width is no wider than as specified, but can have a length that is greater), unless pointed out otherwise.

FIG. 1A schematically shows structure of a biocompatible structure 100 according to certain embodiments of the present disclosure. The biocompatible structure 100 can be in any shape that conforms to a shape of an implant site. For example, the biocompatible structure can have a cylindrical shape, a rectangular shape, or a spherical shape.

Figure 1B:
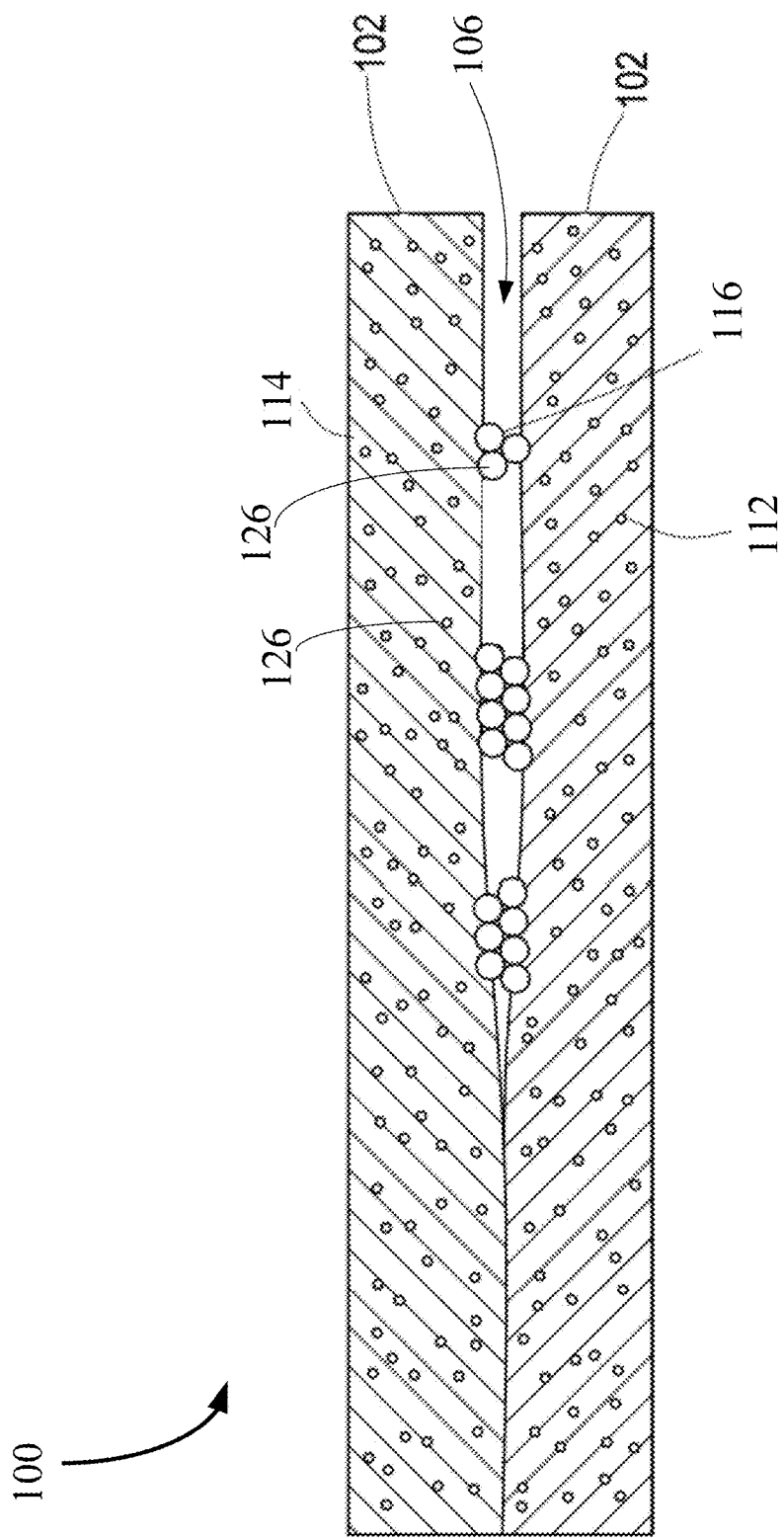
FIG. 1B illustrates a part of a biocompatible structure according to certain embodiments of the present disclosure.

The biocompatible structure includes two or more modified polymer layers 102 stacked together. As will be described below, the modified polymer layers 102 each have nanoparticles 112 dispersed in a polymer matrix 114. In certain embodiments, the nanoparticles 112 are hydroxypatite (HAP) nanoparticles. Further, as shown in FIGS. 1A and 1B, spacer particles 116 are located in between any two of the layers 102 and can function as spacer layer 106 between the polymer layers 102. In certain embodiments, the spacer particles 116 each have a diameter of about 2-100 μm. In certain embodiments, the spacer particles 116 are partially embedded, or trapped, in the surface portion of the polymer layers 102. In certain embodiments, the spacer particles 116 are formed as layers 106, and each spacer layer 106 can have a thickness between approximately 0.001 mm and approximately 50 mm, but are typically less than 3 mm. The layers can be mechanically stacked or applied in situ on top of one another. In certain embodiments, the spacer particles 116 can be bone particles or composite particulates as described below. In certain embodiments, the spacer particles 116 can be HAP particles as described below. In certain embodiments, a portion of a polymer layer 102 can contact a portion of an adjacent polymer layer 102. In certain embodiments, those contacted portions can cross-link with each other. In certain embodiments, a polymer coating 110 encloses the stacked polymer layers 102 and spacer layers 106. Further, the surface of the coating 110 can have trapped spacer particles 116. In certain embodiments, the spacer particles 116 can form a layer and cover a substantial portion of the entire coating 110.

The polymer layers 102 can have different sizes and shapes as desired. In certain embodiments, the polymer layers 102 can be made as strips. For example, the polymer strips 102 each can have a length of 0.005-50 cm, a width of 0.002-50 cm, and a thickness of 0.001-50 mm. The size of the entire structure 100 can vary in order to match the size of the bone defect that needs to be regenerated.

In certain embodiments, the polymer matrix 114 of the modified polymer layer 102 can be polyurethane. The particles 112 dispersed in the polymer matrix 114 can be hydroxypatite (HAP) nanoparticles. The weight percentage of the nanoparticles 112 in the polymer film/layer 102 is defined as the total weight (e.g., grams) of the nanoparticles 112 divided by the total of the weight of the nanoparticles 112 (grams) and the weight of the solid polymers 114 (grams) used for the preparation of the polymer film 102. For example, a total of A grams of nanoparticles 112 and a total of B grams of polymers 114 are used to manufacture a polymer film 102. The weight percentage of the nanoparticles 112 in the polymer film 102 is calculated as A/(A+B). In certain embodiments, the weight percentage of HAP nanoparticles 112 in the polymer layer 102 is about 0.05-95%. In certain embodiments, the weight percentage of HAP nanoparticles 112 in the polymer layer 102 is about 20%.

In certain embodiment, the nanoparticles 112 dispersed in the polymer layer 102 are Hydroxylapatite nanoparticles and can have a dimensional range between 1-100 nanometer (nm). Hydroxylapatite, also called hydroxyapatite (HA or HAP), is a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. Hydroxylapatite is the hydroxyl end member of the complex apatite group. The $OH^-$ ion can be replaced by fluoride, chloride or carbonate, producing fluorapatite or chlorapatite. It crystallizes in the hexagonal crystal system. Pure hydroxylapatite powder is white. Naturally occurring apatites can, however, also have brown, yellow, or green colorations, comparable to the discolorations of dental fluorosis. Up to 50% of bone by weight is a modified form of hydroxylapatite (known as bone mineral). In certain embodiments, the HAP nanoparticles dispersed in the polymer layer can be composed of pure HAP, having significant crystallinity and very good dispensability due to the presence of oxygen groups on the surface.

The presence of HAP nanoparticles 112 in the polymer film 114, among other things, contributes to the pore size and the strength of the polymer film 114. In addition, the concentration of HAP nanoparticles 112 is also related to the degradation rate of the polymer film 114 when the polymer film 114 is used as implant material.

In certain embodiments, the HAP nanoparticles 112 can enhance bone/mineralization in bone cells. The HAP nanoparticles 112, together with other nanomaterials, have the ability to increase the osteogenesis and mineralization in bone cells.

In certain embodiment, the spacer particles 116 between the polymer layers 102 of the present disclosure are bone particles. The bone particles 116 can be autografts, allografts, xenografts (usually bovine) or alloplastic bone grafts (synthetic, such as tricalcium phosphate). In certain embodiment, the bone particles 116 are treated with bone mineral products, or composite particles. Bones from slaughtered animals are an inexpensive raw material available in large quantities to produce bone mineral. Bones typically contain 50 to 60% of very fine crystallites of a form of modified hydroxylapatite, which is bonded by collagenic tissue and contains significant qualities of proteinaceous and other matter as well as associated fat and muscle tissues. Such a modified hydroxylapatite, in a pure state and has its essential crystal structure, represents a highly biocompatible remodeling bone implant material.

In certain embodiments, the bone particles 116 include hydroxyapatite like crystallites with a particular degree of crystallinity, habit, and size (irregular platelike morphology, 5-10 nm in thickness 10-50 nm in length). The specific surface chemistry of the bone particles 116 results from the calcium to phosphate ratio (37.5-38.0% calcium and 15.5-19.0% phosphorus). The inorganic phase of the bone particle 116 contains porosity including ultrastructural interstices (10-100 nm) between the crystallites occurring naturally and produced by removal of the organic phase, and microscopic spaces (1-20 µm) including osteocyte lacunae, canaliculi, vascular channels, volkman's canals, and the canals of haversian systems (100-500 nm). The specific surface area, which is a measure of porosity is in the range 50 to 100 $m^2/gm$ as determined by mercury porosimetry. The crystallinity of the bone particle 116 can be characterized by X-ray diffraction and the porosity and crystallite morphology and size by electron microscopy.

In certain embodiment, the bone particles 116 of the present disclosure are demineralized bone particles 116 purchased from Geistlich BioOss, INC. The bone particles 116 can be of bovine origin and treated such that only the inorganic structure is left, while the organic materials are removed. The bone particles 116 are composed of powder particles with a diameter of 0.01-100 micrometer (µm).

In certain embodiments, the spacer particles 116 can be large particles of HAP that, e.g., are produced in the lab, or composite particles (polymer and inorganic particles).

In certain embodiments, the biocompatible structure 100 can include bioactive materials 126. In certain embodiments, the bioactive materials 126 can be sprayed on the surface of the biocompatible structure 100, and/or incorporated in the polymer structures 102 to promote bone growth.

The bioactive materials 126 can be proteins/peptides, HA, drugs, growth factors, antibiotics (such as tetracycline), and bone morphogenic proteins. Preferred bioactive agents 126 are those that enhance tissue regeneration and/or tissue adhesion. Illustrative examples include growth factors, antibiotics, immuno-stimulators, and immuno-suppressants. In one embodiment, the bioactive agent 126 may be a bone morphogenic protein such as bone morphogenetic proteins (BMP). In another embodiment, the bioactive agent 126 may be a growth factor such as fibroblast growth factors (FGF) or an agent which promotes the generation of connective tissue.

In certain embodiments, tissue can also be grown in vivo by implanting the biocompatible structure 100 and stem cells or other types of suitable cells (liver cells for the growth of liver tissue; myocardial cells, muscle cells for replacing/restoring damaged heart tissue; epithelial cells, connective tissue cells for skin grafts; osteblasts for bone generation) to an implant site. Alternatively, tissue can be grown in vitro on the biocompatible structure 100 and then implanted (for example, for growth of connective tissue/coronary vessels for arterial grafts).

Suitable living cells can be placed in the biocompatible structure before implantation or implanted together with the biocompatible structure 100 into a body. The living cells include epithelial cells (e.g., keratinocytes, adipocytes, hepatocytes), neurons, glial cells, astrocytes, podocytes, mannary epithelial cells, islet cells, endothelial cells (e.g., aortic, capillary and vein endothelial cells), and mesenchymal cells (e.g., dermal fibroblasts, mesothelial cells, osteoblasts), smooth muscle cells, striated muscle cells, ligament fibroblasts, tendon fibroblasts, chondrocytes, fibroblasts, and any of a variety of stem cells. Also suitable for use in the biocompatible structure 100, 200 are genetically modified cells, immunologically masked cells, and the like. Appropriate extracellular matrix proteins (ECM) may be added to the biocompatible structure to further promote cell ingrowth, tissue development, and cell differentiation within the scaffold. ECM proteins can include one or more of fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin.

Additional bioactive agent 126 incorporated in the biocompatible structure 100, among other things, includes biologically active macromolecules helpful for cell growth, morphogenesis, differentiation, and tissue building, include growth factors, proteoglycans, glycosaminoglycans and polysaccharides. These compounds are believed to contain biological, physiological, and structural information for development or regeneration of tissue structure and function.

In certain embodiments, the biocompatible structure 100 can be plasma-treated/activated/electro-sprayed to functionalize the surface of the biocompatible structure 100. Surface treatment can improve the hydrophilicity of the biocompatible structure 100 and promote the colonization of cells and the adhesion of bone particles to the surface and pores of the biocompatible structure 100. The surface can also be functionalized by electron or ion bombardment, laser irradiation and/or by any other physical or chemical surface reaction that affects the bonds near the surface. These processes can also help in sterilization of the implant. Plasma treatment breaks the surface bonds of the polymer. After plasma treatment, oxygen atoms "attach" to the surface, changing the surface energy of the surface such that the surface becomes more hydrophilic and has oxygen and nitrogen rich functional groups.

The biocompatible structure 100 of the present disclosure is highly porous, biocompatible, and allows for vascular ingrowth for bone/tissue regeneration. The surface typically does not inhibit any biological entity from interacting and to be hydrophilic or potentially become hydrophilic under different conditions or processes. Suitable materials for building structures for tissue/bone engineering and regeneration are certain polymers, ceramics, carbon-based materials and metals and metal composites. In certain embodiments, the polymer layers 102 of the biocompatible structure 100 of the present disclosure are formed from polyurethane. In certain embodiments, the biocompatible structure 100 has a layered structure composed of a polymeric material that may contain other substances, such as bioactive substances or substances promoting the generation of tissue growth. Those substances can be formed inside a polymer layer 102 or on the surface of a polymer layer 102. Some of the bioresorbable polymers may or may not require enzymes in order to degrade. The layered, porous design gives this structure a very high surface area for neovascularization and the growth of cells necessary for tissue regeneration. In addition, stem cells, osteoblasts, and other types of suitable cells can be incorporated into the system to aid in tissue generation. The biocompatible structure 100 can assume different shapes and dimensions as may be required for a particular application. The biocompatible structure 100 can be properly positioned in the surgical site directly or with medical pins, screws, or other devices.

The biocompatible structure 100 is configured such that the degradation rate or the resorption rate of the biocompatible structure 100 is substantially matching a rate of tissue generation in the biocompatible structure 100. The controllable degradation rate of the biocompatible structure 100 can also provide controllable release of the bioactive substance or cells formed in the biocompatible structure 100. The polymer may have a different degradation rate than that of the biocompatible structure 100, but it contributes significantly to the degradation rate of the biocompatible structure 100. Accordingly, a polymer with suitable degradation property is chosen to produce the biocompatible structure 100 of the present disclosure.

The polymer layers 102 can be degraded by several mechanisms. The most common mechanism is diffusion. Further, the bioactive substances (agent) of the biocompatible structure can diffuse in various manners. The bioactive agent (drug) can have a core surrounded by an inert diffusion barrier, which can be membranes, capsules, microcapsules, liposomes, and hollow fibers. Alternatively, the active agent can be dispersed or dissolved in an inert polymer. Drug diffusion through the polymer matrix is the rate-limiting step, and release rates are determined by the choice of polymer and its consequent effect on the diffusion and partition coefficient of the drug to be released. By adjusting the diffusion method of the bioactive agent or cells, and components of the biocompatible structure component, suitable rate of bioactive agent or cells is achieved.

In certain embodiments, after implantation the biocompatible structure 100 can be eventually absorbed by the body, for example, by conversion of a material that is insoluble in water into one that is water/liquid-soluble, and thus need not be removed surgically.

In certain embodiments, the polymer layers 102 in the biocompatible structure 100 are biocompatible, processable, sterilizable, and capable of controlled stability or degradation in response to biological conditions. The reasons for designing a biocompatible structure 100 that degrades over time often go beyond the obvious desire to eliminate the need for retrieval. For example, the very strength of a rigid metallic implant used in bone fixation can lead to problems with "stress shielding," whereas a bioresorbable implant can increase ultimate bone strength by slowly transferring load to the bone as it heals. For drug delivery, the specific properties of various degradable systems can be precisely tailored to achieve optimal release kinetics of the drug or active agent.

An ideal biodegradable polymer layer 102 for medical applications typically has adequate mechanical properties to match the application (strong enough but not too strong), does not induce inflammation or other toxic response, may be fully metabolized once it degrades, and is sterilizable and easily processed into a final end product with an acceptable shelf life. In general, polymer degradation is accelerated by greater hydrophilicity in the backbone or end groups, greater reactivity among hydrolytic groups in the backbone, less crystallinity, greater porosity, and smaller finished device size.

A wide range of synthetic biodegradable polymers can be used to form the polymer matrix 102 of the present disclosure, including polylactide (PLA), polyglycolide (PGA), poly(lactide-co-glycolide) (PLGA), poly(e-caprolactone), polydioxanone, polyanhydride, trimethylene carbonate, poly (β-hydroxybutyrate), poly(g-ethyl glutamate), poly(desaminotyrosyl-tyrosine-hexyl ester (DTH)iminocarbonate), poly(bisphenol A iminocarbonate), poly(ortho ester), polycyanoacrylate, and polyphosphazene. There are also a number of biodegradable polymers derived from natural sources such as modified polysaccharides (cellulose, chitin, dextran) or modified proteins (fibrin, casein) that can be used to form the polymer matrix of the present disclosure.

Other materials can be tyrosine-derived polycarbonate poly(DTE-co-DT carbonate), in which the pendant group via the tyrosine—an amino acid—is either an ethyl ester (DTE) or free carboxylate (DT). Through alteration of the ratio of DTE to DT, the material's hydrophobic/hydrophilic balance and rate of in vivo degradation can be manipulated. It was shown that, as DT content increases, pore size decreases, the polymers become more hydrophilic and anionic, and cells attach more readily.

These materials are subject to both hydrolysis (via ester bonds) and oxidation (via ether bonds). Degradation rate is influenced by PEO molecular weight and content, and the copolymer with the highest water uptake degrades most rapidly.

These polymeric materials 102 can also be developed in such a way that they are stable in the biological environment, and degrade only under specific enzymatic conditions (plasmin, etc.). These materials can also include partially expressed fragments of human or animal fibrin such that the system degrades only in contact with plasmin.

The polymer 114 is preferably in solution mixed with a suitable solvent, and other substances can be added to the solution, for example, collagen, drugs, proteins, pep tides, hydroxyapetite crystals (HA), and antibiotics, depending on the type of tissue to be grown. The solution can be sonicated to promote mixing of the constituents.

By chosen a suitable polymer 114, the biocompatible structure 100 can achieve controllable supply of therapeutic, analgesic and/or antibacterial substances, growth factors, proteins, peptides, drugs, tissue subcomponents including but not limited to bone particles and hydroxyappetite, which promote growth, prevent infections and the like.

Figure 2:
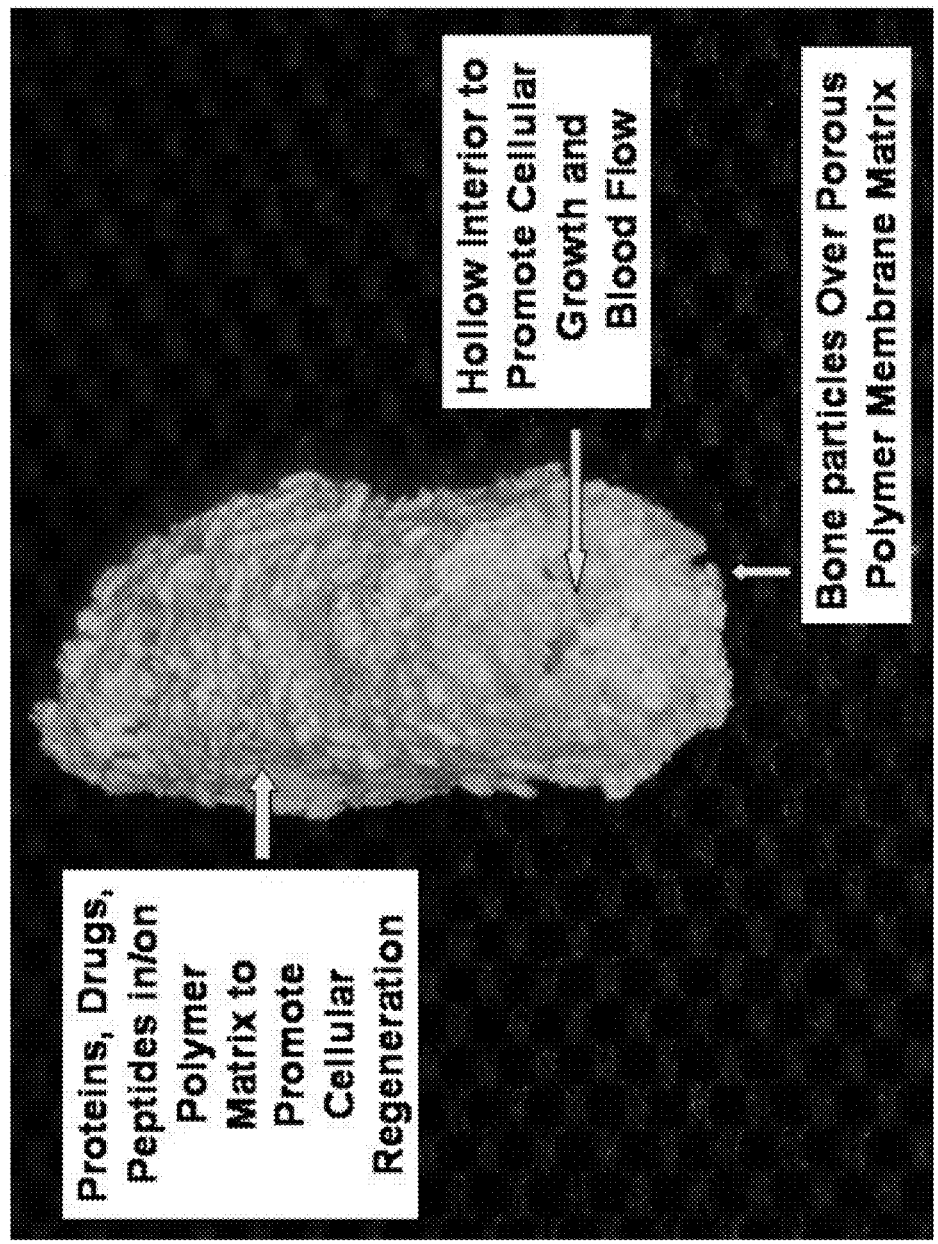
FIG. 2 schematically shows a Scanning Electron Microscopy image of a biocompatible structure at a low resolution according to certain embodiments of the present disclosure.

FIG. 2 schematically shows a Scanning Electron Microscopy image of a biocompatible structure 100 at a low resolution according to certain embodiments of the present disclosure. The biocompatible structure 100 has bone particles 116 over porous polymer membrane matrix and a hollow interior to promote cellular growth and blood flow. In FIG. 2, bioactive materials 126 are shown on the surface of the biocompatible structure 100. In certain embodiments, the bioactive materials 126 can be sprayed on the surface of the biocompatible structure 100, and/or incorporated in the polymer structures 102 to promote bone growth.

Figures 3A, 3B, 3C:
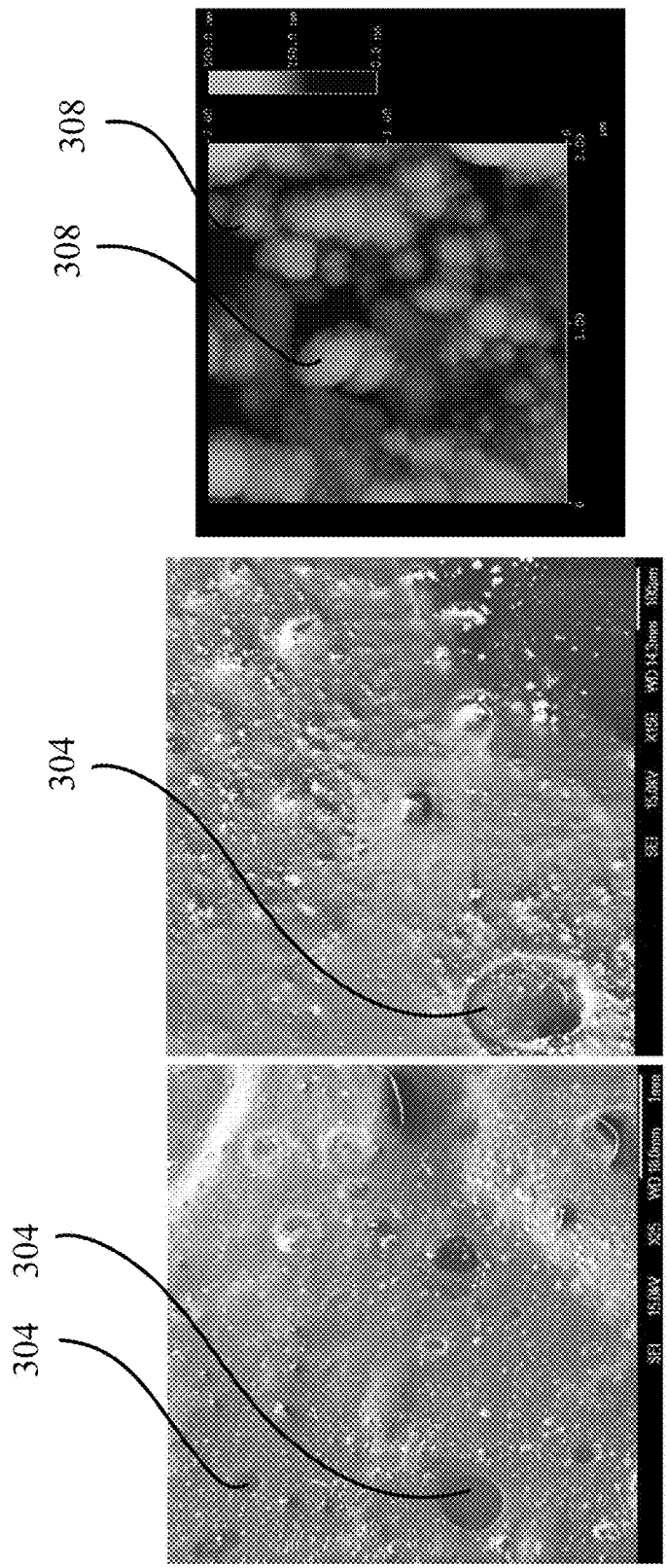
FIGS. 3A-3C schematically show Scanning Electron Microscopy images of a biocompatible structure at a high resolution according to certain embodiments of the present disclosure.

FIGS. 3A-3C schematically shows Scanning Electron Microscopy images of a biocompatible structure 100 at high resolutions according to certain embodiments of the present disclosure. As shown in FIGS. 3A-3C, the surface of the biocompatible structure 100 made from polyurethane polymer and hydroxyapatite nanoparticles can be very rough and can have one or more polymeric pores 304. The polymeric pores 304 typically are large in size. The size of the polymeric pores 304 can be from about 0.001 μm up to about 10 mm. The nanostructural hydroxyapatatite 308 at the surface of the biocompatible structure 300 can have a size of about 1 nm to about 500 nm, and the majority of the nanostructural hydroxyapatite 308 can have a size of about 2 nm to about 300 nm. Inside the biocompatible structure 100 is semi-empty due to the spacing between the layers offered by the bone particles. The pore size should vary both in the range of nanometer (nm) and the range of micrometer (μm).

When placed in an implant site, new tissue of a patient can grow across the pores on the surface of the biocompatible structure, and inside the hollow interior of the biocompatible structure.

In certain embodiments, the biocompatible structure 100 useful for bone and tissue regeneration can be produced by the following procedures: A polymer 114 is dissolved in a solvent to form a first solution. HAP nanoparticles 112 are added to the first solution to form a second solution. The second solution is applied to a surface to form a polymer film on the surface. A weight percentage of the first tissue forming material to the polymer is about 0.5-95%. The polymer film is cut into a plurality of strips 102. The biocompatible structure is formed by stacking the strips 102 and placing bone particle layers 106 in between the strips 102. Then the structure is coated by a coating 110 formed from the second solution, and bone particles 116 are then added onto the surface of the coating 110.

(1) Dissolving a polymer in a solvent to form a first solution.

In certain embodiments, a polymer 114 is dissolved in a solvent to form a first solution. The polymer 114 can be a synthetic biodegradable polymer, a biodegradable polymer derived from natural source, or their mixture. In certain embodiment, suitable synthetic biodegradable polymer may include polyurethane, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, polyphosphazene, or their mixture. In certain embodiments, the biodegradable polymer derived from natural source may include modified polysaccharides (cellulose, chitin, dextran), modified proteins (fibrin, casein), or their mixture.

In certain embodiment, the polymer 114 is an ester-type hydrophilic polyurethane with a linear expansion of 50-65%. The water uptake of the polymer 114 varies with its composition, anywhere from 30-90%. The polymer 114 is thermoplastic. Alternatively, a thermosetting polymer 114 may work equally well. In certain embodiment, the polymer 114 may be mixed with other polymers to control its degradation rate. In certain embodiment, the polymer is a powder with particles having a diameter of about 0.02-50 mm.

The solvent can be methanol or ethanol or any solvent of the polymer used. In certain embodiment, other organic or inorganic solvent (polar aprotic and protic) may also be used. In certain embodiments, the solvent is at least one of acetone, methyl ethyl ketone, nitromethane, n-propanol, n-butanol, isopropanol, propylene carbonate, dymethil sulfoxide, acetonitrile, dimethylformamide, ethyl acetate, and tetrahydrofuran, dichloromethane.

The polymer 114 is evenly distributed in the first solution. In certain embodiment, low power heating can be used to help the dissolution of the polymer in the solvent. In certain embodiments, stirring is used to accelerate the uniform distribution of the polymer in the first solution. In certain embodiment, after complete dissolvation of the solid polymer in the solvent, the first solution has a low viscosity.

(2) Adding a first tissue forming material 112 to the first solution to form a second solution.

The first tissue forming material 112 is then added to the first solution to form a second solution. In certain embodiments, the first tissue forming material 112 may include nanoparticles of hydroxyapatite (HAP), tricalcium phosphates, mixed calcium phosphates and calcium carbonate, bone particles of zenograft, allografts, autografts, alloplastic grafts, or a mixture thereof.

In certain embodiment, the HAP nanoparticles 112 have a dimensional range between 1-100 nm. The HAP nanoparticles 112 can be composed of pure HAP, having significant crystallinity, and having very good dispensability due to the presence of oxygen groups on the surface.

The polymer 114 and the first tissue forming material 112 are evenly distributed in the second solution. In certain embodiments, sonication is used to accelerate the homogenization of the polymer 114 and the first tissue forming material 112 in the second solution.

The weight percentage of the polymer 114 to the first tissue forming material 112 in the second solution is about 20:1 to 2:1. The ratio is related with the characteristics of the produced biocompatible structure 100. The characteristics of the biocompatible structure 100 include resistance to load and stress, porosity, degradation rate, etc. In certain embodiments, the ratio of the polymer 114 to the first tissue forming material 112 can be adjusted to meet requirement of the condition of a patient, including the bone implant position, size, and metabolic rate of the patient.

In certain embodiment, the first polymer 114 is polyurethane and the first tissue forming material 112 is HAP nanopowder containing HAP nanoparticles. The weight ratio of the added dry HAP nanopowder to the dry mass of the added polymer varies according to the purpose of use.

In certain embodiment, as described below in connection with FIGS. 6-7, if the weight ratio of the dry HAP nanopowders to the dry mass of polyurethane is below 25% (i.e., the weight percentage of dry HAP nanopowder in the total weight of dry HAP nanopoder and dry mass of polymer is about 20%), the produced polymer film 102 as described below is strong and hard. If the weight percentage of the dry HAP nanopowders to the polyurethane is above 40%, the produced the polymer film as described below is weak and breaks easily. In certain embodiment, the HAP nanoparticles 112 do not allow a good crosslinking of the polymer strands. Therefore the polymer film produced with a high ratio of HAP nanoparticles 112 is very powdery and breaks very easily.

(3) Applying the second solution to a surface to form a polymer film on the surface.

In certain embodiment, the polymer film is formed by applying the second solution to a surface, and allowing it to dry. In certain embodiment, the second solution can be dried at a room temperature (e.g., 25° C.). In certain embodiment, the second solution is mildly heated to form the polymer film on the surface, for example, at a temperature higher than room temperature (e.g., 25° C.) and lower than 80° C. In certain embodiment, the drying process is under a vacuum condition. In certain embodiment, the surface is a Teflon surface. In certain embodiment, the surface is a polytetrafluoroethylene (PTFE) surface. In certain embodiment, the second solution can be dried on a PTFE surface under vacuum and under mild heat for less than 24 hours to form the polymer film. The thickness of the polymer film can be about 2-10 mm.

(4) Cutting the polymer film into a plurality of strips.

In certain embodiments, the formed polymer film is cut into the plurality of strips. The strips can be any suitable shape and size to produce a biocompatible structure with a predetermined shape and size. In certain embodiment, each of the strips 102 is identical to other strips. In certain embodiment, each of the strips has a length of about 0.002-50 cm, a width of about 0.002-50 cm, and a thickness of about 0.001-50 mm.

(5) Forming the biocompatible structure 100 by the strips, the second solution, and a second tissue forming material.

In certain embodiment, the biocompatible structure 100 is formed from the strips, the second solution, and a second tissue forming material and the following operations:

(a) Constructing a scaffold by stacking the strips to form polymer layers 102 and adding bone particle layers 106 between the polymer layers. In certain embodiments, a strip is disposed on a surface as the first polymer layer 102. A first layer of bone particles 106 is then applied on the first polymer layer 102. A second strip is then used to cover the first bone particle layer 106 to form the second polymer layer 102. By alternatively disposing polymer layers 102 and bone particle layers 106, the scaffold with a predetermined shape and size is constructed. The scaffold structure composed of polymer layer 102 containing HAP nanoparticles 112, bone particle layer 106, polymer layer 102 containing HAP nanoparticles 112, bone particle layer 106 alternatively. In certain embodiments, at least one polymer layer 102 is located as one of the outside layers of the scaffold. In certain embodiment, at least one bone particle layer 106 is located as one of the outside layers of the scaffold. In order for the entire structure to stay together, methanol or other solvent of the polymer is added by, for example pipetting, to superficially liquefy the polymer layers 102, such that the bone particles 116 can be "trapped" in the polymer layers 102 when the structure dries. The bone particles 116 can be partially embedded in the polymer layers 102. After the polymer layers 102 re-solidifies, the bone particle layers 106 are connected with the polymer layers 102.

(b) Applying the second solution to the scaffold to form a coated scaffold. In certain embodiments, the scaffold built as described above is then coated by covering with a polymer film that is in a liquid form. In certain embodiment, the second solution is a sticky solution before applying to the scaffold. In certain embodiment, part of the second solution poured on the surface of the scaffold penetrates to the inside of the scaffold. The poured second solution forms a coat 110 on the surface of the scaffold and helps to hold the components of the scaffold together.

(c) In certain embodiment, the forming operation further includes adding the second tissue forming material to the coated scaffold to form the biocompatible structure 100. In certain embodiment, the second tissue forming material can be nano-sized bone particles, micro-sized bone particles, or a mixture thereof. The structure is then allowed to dry overnight under vacuum and mild heat to form the biocompatible structure according to the present disclosure.

The biocompatible structure 100 can be any shape and size such that the biocompatible structure matches the size of the bone defect that needs to be regenerated. In certain embodiment, the biocompatible structure has a cylindrical shape or a spherical shape. In certain embodiment, the length of the biocompatible structure is about 2.5 cm (1 inch) and the diameter is about 0.1-1 cm, which matches the diameter of the bone that needs to be replaced.

In certain embodiment, the method further includes subjecting the biocompatible structure 100 to plasma treatment. For example, once completely dried, the biocompatible structure 100 is placed into glass vials for storage. The biocompatible structure 100 is plasma treated by a radio frequency (RF) plasma discharge device, under an environment of oxygen, nitrogen or a mixture of oxygen and nitrogen. In certain embodiment, the RF plasma treatment time is about 1-3 minutes. In certain embodiment, the plasma treated biocompatible structure 100 is sterilized and sent for animal studies. The purpose of the plasma treatment is to break the surface bonds of the polymer. After plasma treatment, oxygen atoms "attach" to the surface, changing the surface energy of the surface such that the surface becomes more hydrophilic and has oxygen and nitrogen rich functional groups.

In certain embodiment, the method of manufacturing the biocompatible structure 100 further includes adding a third tissue forming material to the biocompatible structure 100. In certain embodiment, the third tissue forming material includes a bioactive material, cells, or a mixture thereof. The bioactive material includes proteins, enzymes, growth factors, amino acids, bone morphogenic proteins, platelet derived growth factors, vascular endothelial growth factors, or a mixture thereof. The cells includes epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof.

The biocompatible structure 100 can be any shape, size and weight to fit with an implant site. In certain embodiment, long bones were surgically removed from the tibia of goats, and biocompatible structures conform to the implant sited of the goats according to the present disclosure are used for bone regeneration of the goats.

In certain embodiment, when the biocompatible structure 100 is used in dental applications for bone generation, the concentration of HAP nanoparticles can be much higher than the concentration of HAP nanoparticles in the biocompatible structure for some other bone regeneration, for example, tibia regeneration. In certain embodiment, the biocompatible structure for dental applications can be crumbled and forms a lot of particles with high surface area.

In certain embodiment, instead of manufacturing the biocompatible structure 100 and then using it as implant material, the biocompatible structure 100 can also be formed in situ. For example, a first polymer layer is air sprayed at an implant site or a bone defect area, a first layer of bone particles is then added to the polymer layer and deposits on the polymer layer. After that, a second polymer layer is air sprayed on the first bone particle layer, followed by adding a second layer of bone particles. The process is repeated until the biocompatible structure, including alternating polymer layers and bone particle layers, matches the implant site or mimics the bone defect that needs to be replaced.

In certain embodiment, a Doctor of Medicine (MD) can take a 3D computer axial tomography scan (CAT) of a patient and sent the result for example by emailing the CAT scan file to a manufacturer. The manufacturer then can build the implant according to the present disclosure to perfectly match the actual bone defect.

Figure 4:
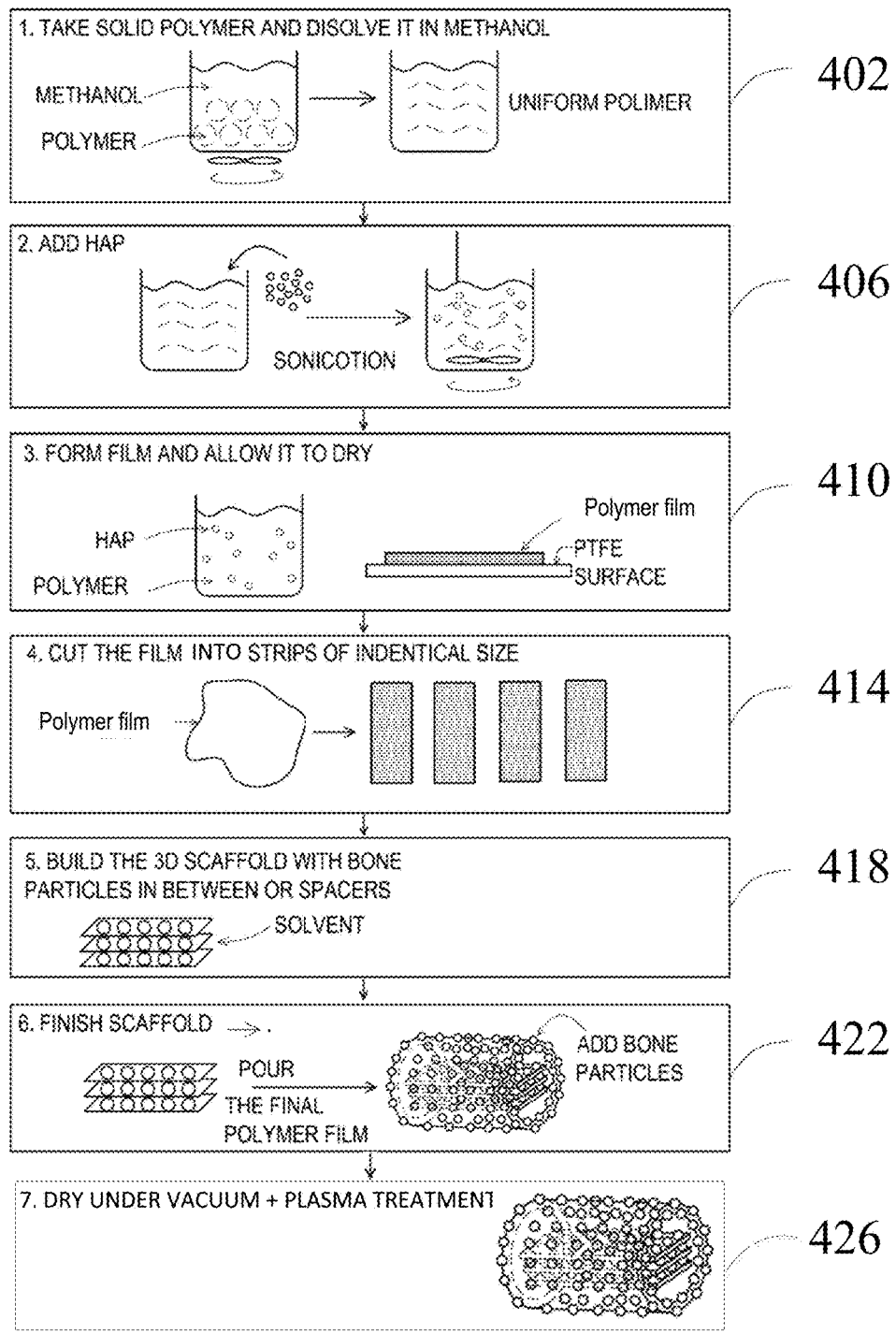
FIG. 4 schematically shows procedures for producing a biocompatible structure according to certain embodiments of the present disclosure.

FIG. 4 illustrates an example of preparing a biocompatible structure 400 according to certain embodiments of the present disclosure.

In operation 402, 500 ml methanol is added to a 1 L beaker. The beaker is placed on a magnetic stirrer and a magnetic stir bar is used for mixing. 80 grams polyurethane 114 is then added to the methanol in the beaker. The solution is mixed by the stirring bar to completely dissolve the polyurethane in the methanol solvent and uniformly distributed the polyurethane 114 in the solution. The mixing and dissolving of polyurethane is at room temperature. In certain embodiment, the solution can be heated to accelerate the process.

In operation 406, 20 gram HAP nanoparticles 112 (e.g., Berkeley Advanced Biomaterials, Inc.) is then added to the solution. Sonication is applied to guarantee the evenly distribution of the HAP nanoparticles 112 in the solution.

In operation 410, 10 ml of the solution is pipetted from the beaker and applied to a PTFE surface. A thin layer of solution is formed on the PTEF surface. The thin layer of solution is allowed to dry at room temperature for variable times to form a polymer film. Alternatively, the layer of solution on the PTFE surface can be placed in an oven to heat or low pressure for a period of time to accelerate the formation of the polymer film. In certain embodiment, the temperature can be about 30-70° C., and the period of time for the heating is about 2-1500 minutes. In certain embodiment, the second solution is allowed to dry on a PTFE surface under vacuum under mild heat for less than 24 hours to form the polymer film. The thickness of the polymer film can be about 0.01-50 mm.

In operation 414, the polymer film is then cut into identical strips with a length of about 0.05-20 cm, a width of about 0.02-5 cm, and a thickness of about 0.01-50 mm. In certain embodiment, the polymer film can be cut into strips with varies shape and size.

In operation 418, a first strip is placed on the PTFE surface to form a first polymer layer 102. A first layer of bone particles 106 is added on the surface of the first polymer layer 102. A second strip is placed onto the first bone particle layer 106 to form a second polymer layer 102. Then a second bone particle layer 106 is formed on the second polymer layer 102. By alternatively disposing the strips and the bond particle layers, a three-dimensional scaffold is formed with a predetermined shape and size.

In order for the entire structure to stay together, methanol or other solvent of the polymer is added by, for example pipetting, to superficially liquefy the polymer layers 102, such that the bone particles 116 can be "trapped" in the polymer layers 102 when the structure dries. The bone particles 116 can be partially embedded in the polymer layers 102. After the polymer layers 102 re-solidifies, the bone particle layers 106 are connected with the polymer layers 102. Alternatively, after adding each bone particle layer 106, the methanol or other solvent can be added to trap or embed the bone particles 116 in the corresponding polymer layers 102.

Next, 1 ml of the methanol/polyurethane/HAP nanoparticle solution is added to the surface of the three-dimensional scaffold and allowed to dry. Accordingly, a coating 110 is formed on the surface of the three-dimensional scaffold. In certain embodiment, the coating 110 not only covers the outside of the three-dimensional scaffold, but also can penetrate to the inside of the three-dimensional scaffold.

Further, bone particles 116 or other suitable particles may be added to the surface of the coating 110.

In operation 422, the structure is then dried under vacuum overnight. In certain embodiment, the structure is further subjected to plasma treatment.

A series of biocompatible structures 100 is produced according to the above example by varying the HAP concentration. The HAP concentration in the polymer film is closely related with the characters of the produced biocompatible structure 100.

Figure 5A:
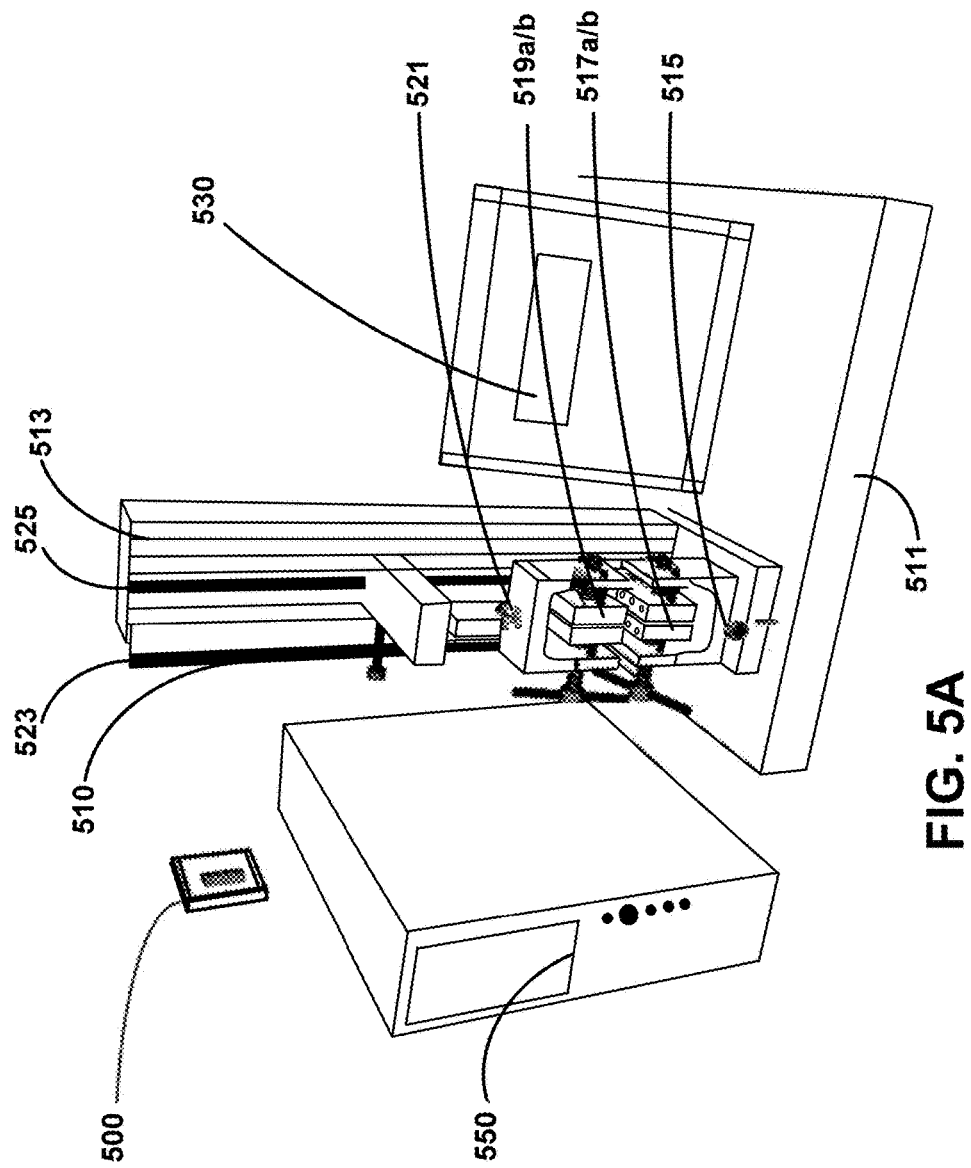
FIGS. 5A and 5B schematically show a pull test set up for measuring maximum load and maximum stress of polymer films according to certain embodiments of the present disclosure.
Figure 5B:
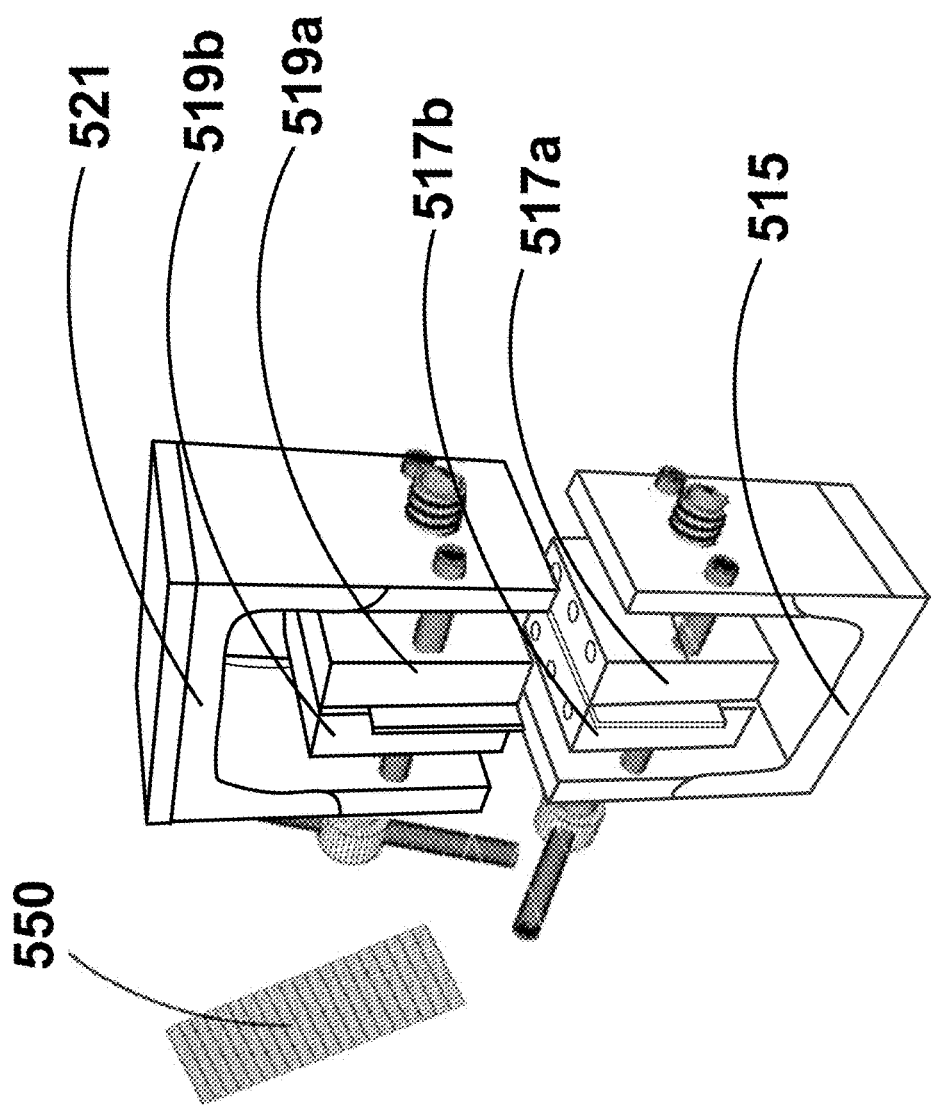

FIGS. 5A and 5B show a pull test system 500 used to measure the maximum load and maximum stress of polymer films 550 with various concentrations of polyurethane and HAP nanoparticle in accordance with certain embodiments of the present disclosure. In one example, the mechanical behavior of the composites was analyzed using an ADMET 7600 EXPERT single-column, universal, electromechanical testing machine. The instrument performs a "pull test" by stretching the polymer film in its axial direction and instantaneously produces a "csv" file using the eP2 Digital Controller and Gauge Safe Basic Testing Software. The pull test system 500 includes a pull test structure 510, a digital controller 530 and, optionally, a computer 550. The pull test structure 510 has a base 511, a column 513 fixed to and perpendicular to the base 511, a bottom head 515 connected with two bottom grips 517 a and 517 b facing each other, a top head 521 connected with two top grips 519 a and 519 b facing each other, a scale 523 attached to the column 513, and a rail 525 placed in the column 513. At least one of the top head 521 and the bottom head 515 is connected with the rail 525 and is movable along the rail 525. In this embodiment, the top head 521 is connected through a chain or a cable to a motor (not shown) and the chain or the cable pulls/drives the top head 521 along the rail 525. The top grips 519 a/519 b move together and at the same speed with the top head 521.

Polymer films 550 were prepared and tested. In certain embodiment, the polymer films 550 contain various concentrations of polyurethane and HAP nanoparticles. In one embodiment, the weight percentage of the HAP nanoparticles in the polymer films are 0%, 0.5%, 1%, 2%, 3%, 5%, 10%, 15%, 20% and 30% respectively. As described above, the weight percentage of the HAP nanoparticles is defined as the weight of the HAP nanoparticle powder (in gram) used for preparing the polymer film divided by the total weight of HAP nanoparticle powder (in gram) and solid polymers (in gram) used for preparing the polymer film 550. The polymer films 550 used in the test have predetermined dimensions. In certain embodiments, the size of the polymer films 550 is 6 cm×1.5 cm×0.02 cm. In certain embodiment, polymer films with the same concentration of HAP nanoparticles are prepared with different sizes for testing. During the maximum load and maximum stress testing process, the top grips 521 a/521 b and the bottom grips 517 a/517 b clip two ends of the polymer film 550 in the longitudinal direction of the polymer film 550. The dimension of the polymer film 550 and the parameters of the force to be used are entered into the digital controller 530. In certain embodiments, the length of the polymer film used in the calculation is an effective length, for example, measured by the scale, from the bottom edges of the top grips 519 a/519 b to the top edges of the bottom grips 517 a/517 b. In certain embodiments, if the polymer film 550 clipped between the top grips 5191/b and the bottom grips 517 a/b has a dog bone shape, the length used for calculation is the narrow portion of the dog bone shape. When the testing starts, the motor moves at least one of the top head 521 and the bottom head 515, for example, the top head 521. The top grips 519 a/519 b move together and at the same speed with the top head 521 to pull the polymer film 550 at a predetermined speed. In certain embodiment, the speed can be 0.01-2.5 mm per minute. The top grips 519 a/519 b move along the rail 525 at a predetermined speed to pull the polymer film 550 until the polymer film 550 breaks. The original dimensions of the polymer film 550, the moving speed of the top grips 519 a/519 b, the length of the polymer film 550 immediately before it breaks are recorded. The maximum load and the maximum stress are calculated. In certain embodiments, the calculation is performed by a processor (not shown) in the computer 550. The maximum load is the pull force (newton) applied to the polymer film 550 when the polymer film breaks. The maximum stress (KPa) is the pull force applied to the polymer film 550 when the polymer film 550 breaks divided by the cross-sectional area of the polymer film 550 (the original width times the original thickness of the polymer film 550).

The load and stress tests are performed for the polymer films 550 made according to the present disclosure. In certain embodiments, the polymer films contain various concentrations of polyurethane and HAP nanoparticles.

Figure 6:
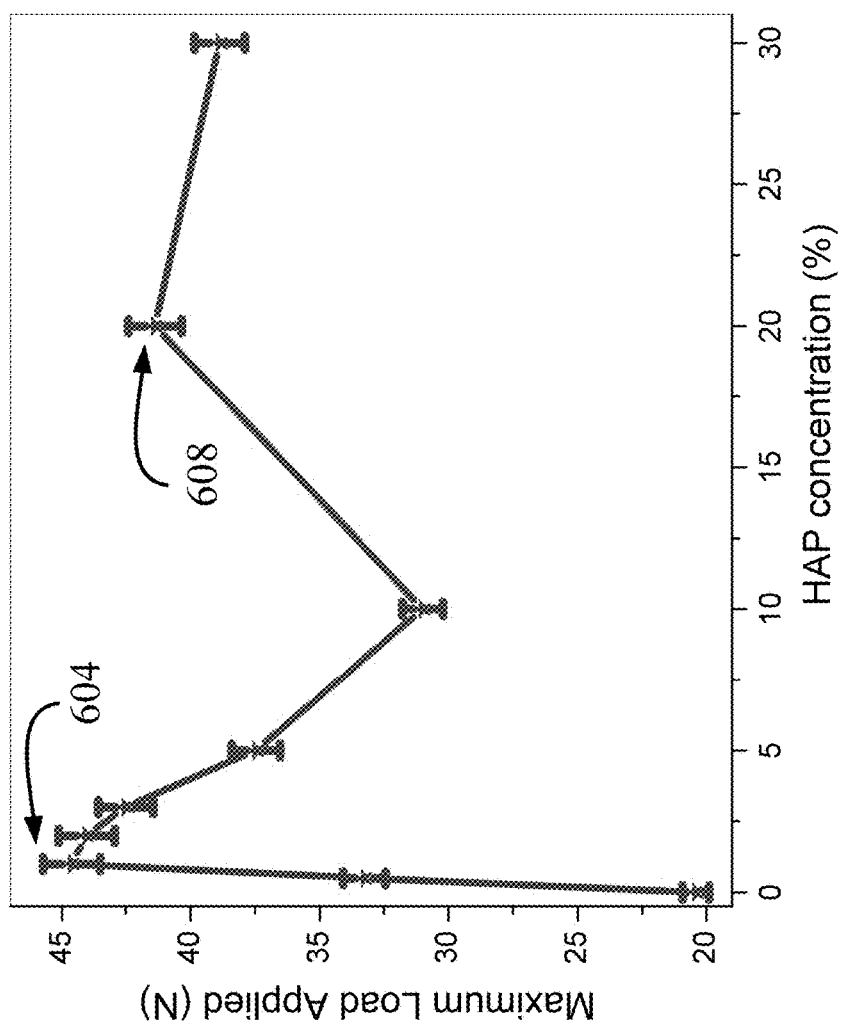
FIG. 6 schematically shows maximum load of the polymer films according to certain embodiments of the present disclosure.

FIG. 6 is a load graph of the polymer films 550 in a two dimensional coordinate system, which shows a functional relationship between the weight percentage of the HAP nanoparticles in a polymer film and a maximum load of that polymer film. The X-axis of the coordinate system is the weight percentage of the HAP nanoparticles and the Y-axis of the coordinate system is the maximum load of the polymer film. As shown in FIG. 6, the maximum load (in newton) for the polymer films 550 containing 0%, 0.5%, 1%, 2%, 3%, 5%, 10%, 20% and 30% of HAP nanoparticles are measured and calculated. The maximum load increases sharply from about 20 newton (N) to about 44 N when the HAP concentration increases from 0% to about 1%. Then the maximum load drops to about 31 N when the HAP concentration increases from 1% to around 10%. After that, the maximum load increases again to about 41 N at around 20% HAP concentration and drops to about 38 N at around 30% HAP concentration. Thus, the load graph has two peaks corresponding to 1% and around 20% of HAP concentration. In certain embodiment, the second peak at around 20% HAP concentration in the load graph is named load peak.

Figure 7:
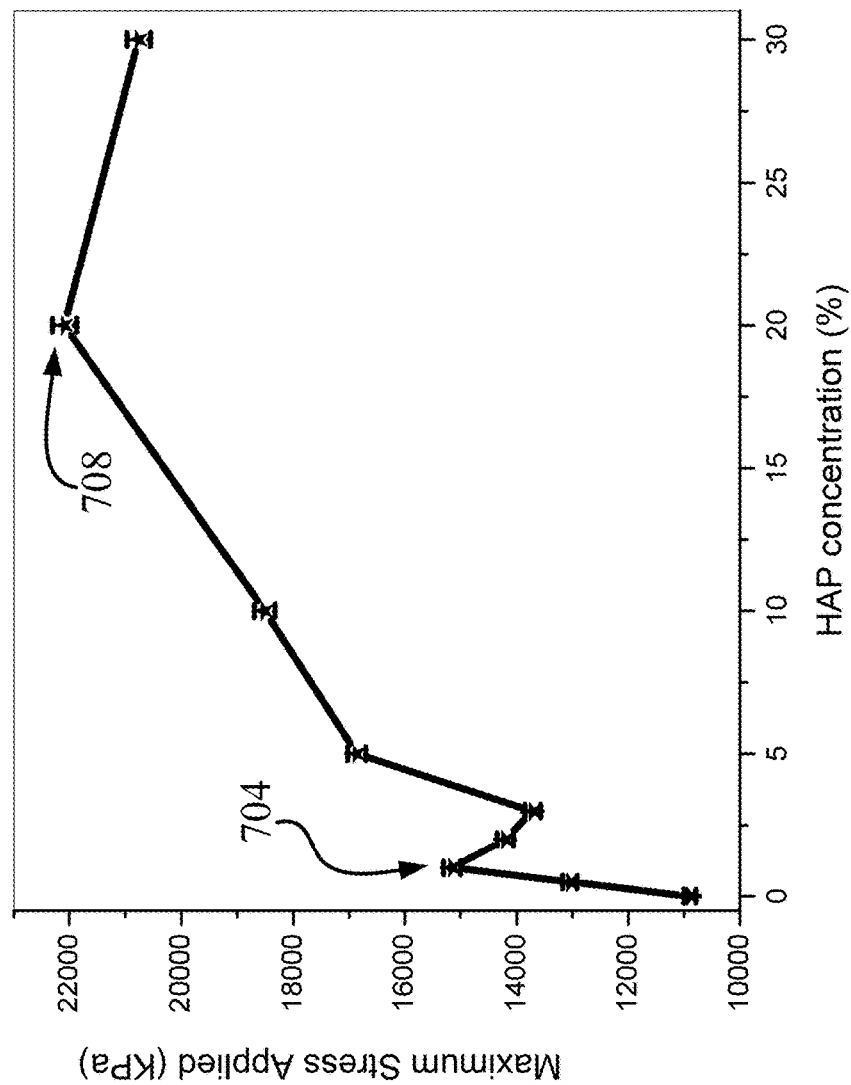
FIG. 7 schematically shows maximum stress of the polymer films according to certain embodiments of the present disclosure.

FIG. 7 is a stress graph of the polymer films 550 in a two dimensional coordinate system, which shows a functional relationship between the weight percentage of the HAP nanoparticles in a polymer film and a maximum load of that polymer film. The X-axis of the coordinate system is the weight percentage of the HAP nanoparticles and the Y-axis of the coordinate system is the maximum stress of the polymer film 550. As shown in FIG. 7, the maximum stress (in KPa) for the polymer films containing 0%, 0.5%, 1%, 2%, 3%, 5%, 10%, 20% and 30% of HAP nanoparticles are measured and calculated. The maximum stress increases from about 11,000 KPa to about 15,000 KPa when the HAP concentration increases from 0% to about 1%. Then the maximum stress decreases to about 13,600 KPa when the HAP concentration increases from 1% to about 3%. After that, the maximum stress increases to about 22,000 KPa when the HAP concentration increases from about 3% to about 20%. Further increasing HAP concentration in the polymer films from about 20% to 30% can result in decreasing of the maximum stress from 22,000 to about 20,800 KPa. Thus, the stress graph has two peaks corresponding to 1% and 20% of HAP concentration. In certain embodiment, the second peak at 20% HAP concentration in the stress graph is named stress peak.

In certain embodiments, a computer 550 can be used to calculate optimal weight percentage of HAP in the polymer film 550 according to the above load and stress graphs of a series of polymer films 550. The computer 550, utilizing one or more CPUs, can receive the data from the pull test structure 510 and the digital controller 530, run a calculation software, and then present the result on a monitor.

An optimal weigh percentage of HAP in the polymer film 550 is determined based on the results from the load graph and the stress graph by the computer 530. In certain embodiments, both the load graph and the stress graph have at least two peaks. The first peak 604 in the load graph corresponding to a lower HAP concentration, and the second peak 608 in the load graph corresponding to a higher HAP concentration. The first peak 704 in the stress graph corresponding to a lower HAP concentration, and the second peak 708 in the stress graph corresponding to a higher HAP concentration. The second peak 608 in the load graph is named load peak 608, and the second peak 708 in the stress graph is named stress peak 708. The peak values from the load peak 608 and the stress peak 708 are extracted. In this example, both of the load peak 608 and the stress peak 708 correspond to a HAP weight percentage (HAP concentration) of 20%. The maximum value and the minimum value of the load peak 608 and the stress peak 708 are determined. In this example, both the maximum value and the minimum value are 20%. The optimal concentration range has an upper limit value and a lower limit value. The upper limit value is the maximum value plus a first predetermined value. The lower limit value is the minimum value minus a second predetermined value. Each of the first predetermined value and the second predetermined value can be, for example, 10%, 5%, or 0%. Accordingly, in this example, the optimal concentration range of the HAP in the polymer film is 10%-30%, preferably 15%-25%, and more preferably 20%.

In another example, the load peak 608 and the stress peak 708 have different values. For example, the load peak may be at 17.5% and the stress peak may be at 22.5%. Accordingly, the maximum value is 22.5% and the minimum value is 17.5%. With the first and second predetermined values at about 10%, preferably 5%, and more preferably 0%, the optimal concentration ranges of the HAP weight percentage in the polymer film are 7.5%-32.5%, preferably 12.5%-27.5%, and more preferably 17.5%-22.5%. Accordingly, any HAP concentration in the above ranges can be chosen as an optimal concentration. In other embodiments, the first and second predetermined values can be different values.

In certain embodiments, according to the results shown in FIGS. 6 and 7, the polymer film with 20% HAP concentration shows good structure stability and strength.

In certain embodiments, the biocompatible structure 100 prepared according to the present disclosure for the treatment of animals and/or humans. In certain embodiment, long bones were surgically removed from the tibia of goats. For generating long bones of these goats, biocompatible structures of a weight about 1.0-2.5 grams (g) were used. For example, 10 implants with the weight of 2.39 g, 2.34 g, 2.11 g, 1.86 g, 2.135 g, 2.18 g, 1.55 g, 2.5 g, 1.22 g, and 1.69 g, respectively, were used to generate long bones for the goats with surgically removed tibia part. For the above 10 examples, the biocompatible structure was made by using 4.52 g of polymer (polyurethane), 0.45 g of HAP nanoparticles, and 15 g of bone particles.

The bone growth using the biocompatible structures 100 according to embodiments of the present disclosure has maturity and integrity.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A method of treating bone deficiencies, comprising applying a biocompatible structure to an implant surgical site, wherein the biocompatible structure comprises:
   a plurality of polymer layers stacked to have a predetermined shape, wherein each of the polymer layers is formed with a polymer and first tissue forming nanoparticles;
   a plurality of bone particle layers disposed between each of two neighboring polymer layers of the plurality of polymer layers;
   a coating surrounding the plurality of polymer layers and bone particle layers; and
   a plurality of second tissue forming particles attached to an outer surface of the coating.

2. The method of claim 1, wherein the biocompatible structure is formed by:
   dissolving the polymer in a solvent to form a first solution;
   adding the first tissue forming nanoparticles to the first solution to form a second solution wherein a weight percentage of the first tissue forming nanoparticles to the polymer is about 0.01-95%;
   applying the second solution to a surface to form a polymer film on the surface, wherein the first tissue forming nanoparticles are dispersed in the polymer film;
   dividing the polymer film into strips;
   constructing a scaffold by stacking the strips to form polymer layers and adding bone or composite particles between the polymer layers;
   applying the second solution to the scaffold to form the coating surrounding the scaffold; and
   adding the plurality of second tissue forming particles to the coating to form a second tissue forming particle layer surrounding the coating, so as to obtain the biocompatible structure.

3. The method of claim 2, wherein the biocompatible structure is further formed by, after adding the plurality of second tissue forming particles to the coating, plasma treating the scaffold surrounded with the coating and the second tissue forming particle layer.

4. The method of claim 2, wherein the surface is a polytetrafluoroethylene (PTFE) surface.

5. The method of claim 2, wherein the plurality of second tissue forming particles comprise nano-sized bone particles, micro-sized bone particles, or a mixture thereof.

6. The method of claim 2, wherein each of the strips has a length of about 0.005-50 centimeter, a width of about 0.002-50 centimeter, and a thickness of about 0.001-500 millimeter, and the biocompatible structure is in a cylindrical shape or a spherical shape.

7. The method of claim 2, wherein the biocompatible structure is further formed by adding a third tissue forming material to the biocompatible structure,
   wherein the third tissue forming material comprises a bioactive material, cells, or a mixture thereof;

wherein the bioactive material comprises proteins, enzymes, growth factors, amino acids, bone morphogenic proteins, platelet derived growth factors, vascular endothelial growth factors, or a mixture thereof; and wherein the cells comprise epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof.

8. The method of claim 1, wherein the predetermined shape is configured to conform to the implant surgical site.

9. The method of claim 1, wherein a weight percentage of the first tissue forming nanoparticles to the polymer is about 0.05-95% such that a resorption rate of the biocompatible structure substantially matches a rate of tissue generation in the biocompatible structure.

10. The method of claim 9, wherein the weight percentage of the first tissue forming nanoparticles to the polymer is about 20%.

11. The method of claim 9, wherein the weight percentage of the first tissue forming nanoparticles to the polymer is about 25%.

12. The method of claim 1, wherein the polymer comprises a synthetic biodegradable polymer, a biodegradable polymer from a natural source, or a mixture thereof; and wherein the synthetic biodegradable polymer comprises polyurethane, polylactide (PLA), polyglycolide (PGA), poly(lactide-co-glycolide) (PLGA), poly(e-caprolactone), polydioxanone, polyanhydride, trimethylene carbonate, poly($\beta$-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, polyphosphazene, or a mixture thereof.

13. The method of claim 1, wherein the first tissue forming nanoparticles comprise nanoparticles of hydroxypatites, tricalcium phosphates, mixed calcium phosphates and calcium carbonate, bone particles of zenograft, bone particles of allografts, bone particles of autografts, bone particles of alloplastic grafts, or a mixture thereof.

* * * * *